United States Patent [19]
LaPointe

[11] Patent Number: 6,146,368
[45] Date of Patent: Nov. 14, 2000

[54] DIAPER TO ELIMINATE BED SORES

[76] Inventor: Lynn LaPointe, 10667 Oak La., Apt. 18104, Belleville, Mich. 48111

[21] Appl. No.: 09/410,597

[22] Filed: Oct. 1, 1999

[51] Int. Cl.[7] .............................. A61F 13/15; A61F 5/00; A61F 13/00; A61F 15/00; A61F 5/48

[52] U.S. Cl. ...................... 604/385.1; 604/348; 604/369; 602/3; 602/43; 602/67; 128/885

[58] Field of Search ................................ 604/385.1, 348; 128/885; 602/3, 43, 67; 119/714, 838, 164, 169, 170, 171

[56] References Cited

U.S. PATENT DOCUMENTS

| | | | |
|---|---|---|---|
| 4,055,180 | 10/1977 | Karami | 128/287 |
| 4,962,769 | 10/1990 | Garcia | 128/889 |
| 5,026,363 | 6/1991 | Pratt | 604/385.1 |
| 5,137,525 | 8/1992 | Glassman | 604/385.1 |
| 5,207,663 | 5/1993 | McQueen | 604/385.1 |
| 5,234,421 | 8/1993 | Lowman | 604/385.1 |

*Primary Examiner*—John G. Weiss
*Assistant Examiner*—Paul Shanoski
*Attorney, Agent, or Firm*—Bliss McGlynn, P.C.

[57] ABSTRACT

A diaper to eliminate bed sores includes a front section, a back section and a middle section extending longitudinally between the front section and the back section. The middle section includes a liquid-permeable inner sheet, a liquid-impermeable outer sheet aligned with and secured to the inner sheet, and an absorbent body disposed between the inner sheet and the outer sheet. The middle section includes an aperture extending through the inner sheet and the absorbent body and the outer sheet and having a thickened portion completely surrounding the aperture. The aperture is adapted to be located over a bed sore on a body of person with the middle portion disposed between legs of the person and the front section disposed in front of the person and the back section disposed in back of the person and attached to the front portion when the diaper is in use.

8 Claims, 2 Drawing Sheets

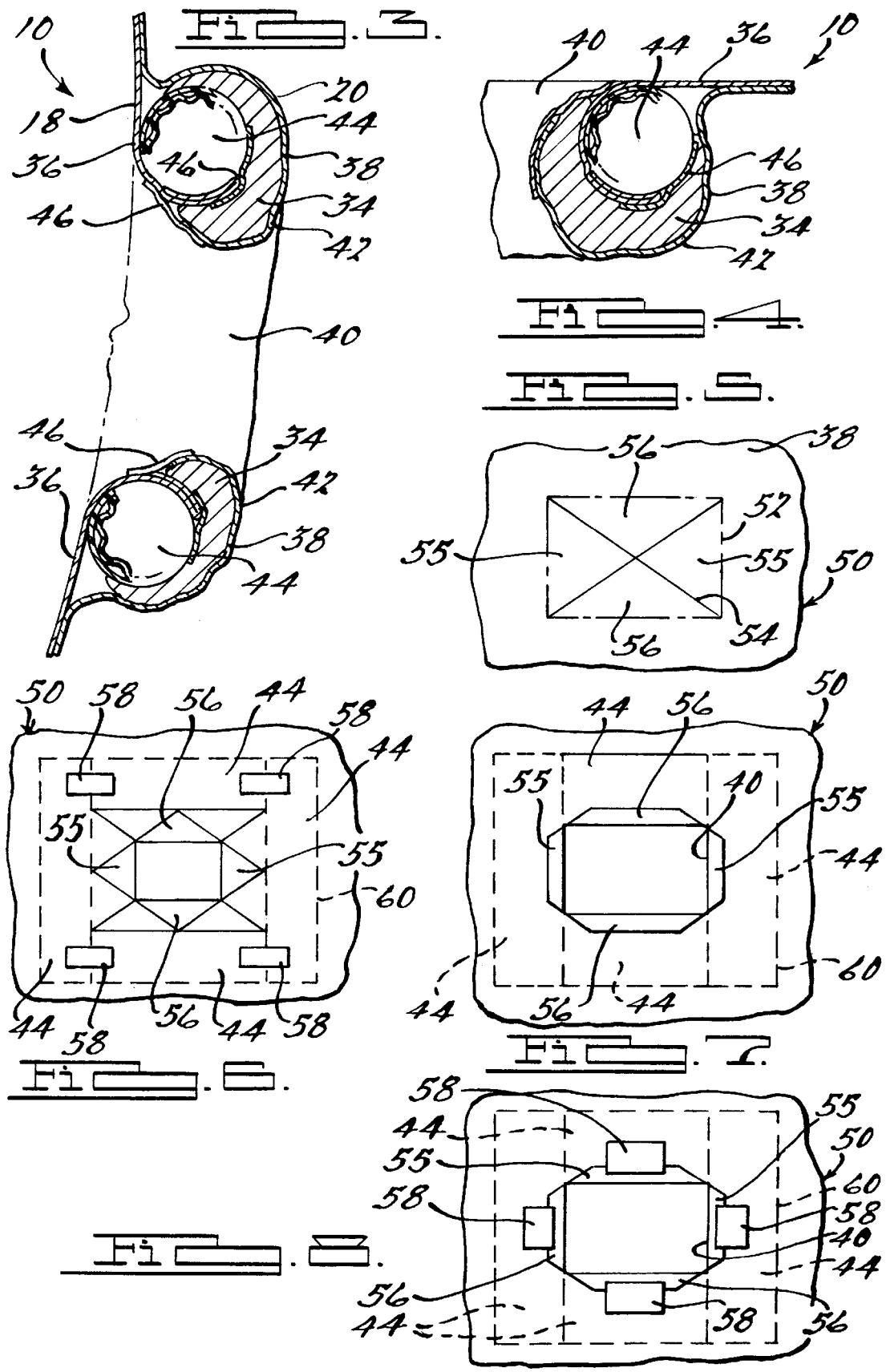

DIAPER TO ELIMINATE BED SORES

BACKGROUND OF THE INVENTION

1. Field of the Invention

The present invention relates generally to diapers and, more specifically, to a diaper to eliminate bed sores.

2. Description of the Related Art

People who are confined to a bed or chair for a long time frequently develop decubitus ulcers, or bed sores, due to forces between their skin and the bed—more accurately, the sheets of the bed—or chair. Specifically, bed sores result from the continuous pressure and friction over extended periods of time exerted on the skin and underlying tissues between the person's bones and the bed or chair. Such pressure and friction, resulting in the interruption of blood flow to the skin, progressively break down and destroy the soft tissue. These sores can be extremely painful and highly susceptible to bacterial infections, thereby impeding the healing process. As a result, it is desirable to prevent bed sores.

In the past, many devices have attempted to permit healing of bed sores by minimizing or eliminating the pressure and friction exerted on the sores. For example, U.S. Pat. No. 4,962,769 to Garcia discloses the use of bubble packaging film for relieving decubitus ulcers or pressure ulcers. In this patent, a body fluid absorbing cushion includes a laminate structure with at least three layers, including an inner water absorbent layer, a center layer consisting of an array of generally closely spaced enclosures defining air supported closed cells, and an outer generally water impervious layer. The array of cells includes a number of cells with varying diameters, wherein the center cells of relatively larger diameter are disposed where forces are greater and radially outwardly positioned cells are of relatively reduced diameter.

Additionally, U.S. Pat. No. 5,462,519 to Carver discloses a bed sore pad. In this patent, a stratiform pad contains a median layer, a body-contacting layer, and a bed-contacting layer. The median layer is a closed cell air bubble film in which series of airtight spaced apart air cells are encapsulated in a strong plastic film, to provide a cushioning effect. The body-contacting layer is composed of stabilizing tape, which is bonded to the upper surface of the median layer by an adhesive layer. The bed-contacting layer is preferably a non-slip siliconized cloth tape having an adhesive coated on the side contacting the median layer. The pad has an interior aperture for surrounding and receiving the bed sore and avoiding contact of the sore with the pad.

Nevertheless, these devices lack a configuration that accomplishes minimization or elimination of the pressure and friction exerted on the sores while allowing air to flow around the sores and to absorb body fluids. Thus, there is a need in the art to provide a diaper for eliminating bed sores.

SUMMARY OF THE INVENTION

It is, therefore, one object of the present invention to provide a diaper to eliminate bed sores.

To achieve the foregoing object, the present invention is a diaper to eliminate bed sores includes a front section, a back section and a middle section extending longitudinally between the front section and the back section. The middle section includes a liquid-permeable inner sheet, a liquid-impermeable outer sheet aligned with and secured to the inner sheet, and an absorbent body disposed between the inner sheet and the outer sheet. The middle section includes an aperture extending through the inner sheet and the absorbent body and the outer sheet and having a thickened portion completely surrounding the aperture. The aperture is adapted to be located over a bed sore on a body of person with the middle portion disposed between legs of the person and the front section disposed in front of the person and the back section disposed in back of the person and attached to the front portion when the diaper is in use.

One advantage of the present invention is that a new diaper is provided for eliminating bed sores on persons. Another advantage of the present invention is that the diaper has a thickened portion that elevates the sore and surrounding skin away from the bed or chair. Yet another advantage of the present invention is that the diaper has a liquid-permeable bottom sheet which absorbs moisture, preventing contact of the skin with moisture that is trapped about the thickened portion that could cause the skin to decay.

Other objects, features, and advantages of the present invention will be readily appreciated as the same becomes better understood after reading the subsequent description taken in connection with the accompanying drawings.

BRIEF DESCRIPTION OF THE DRAWINGS

FIG. 3 is a sectional view taken along line 3—3 of FIG. 2.

FIG. 4 is a sectional view taken along line 4—4 of FIG. 2.

FIG. 5 is a top view of a portion of the diaper for eliminating bed sores illustrating a first step of a method, according to the present invention.

FIG. 6 is a view similar to FIG. 5 illustrating a second step of the method of the present invention.

FIG. 7 is a view similar to FIG. 5 illustrating a third step of the method of the present invention.

FIG. 8 is a view similar to FIG. 5 illustrating a fourth step of the method of the present invention.

DESCRIPTION OF THE PREFERRED EMBODIMENT(S)

Figure 1:
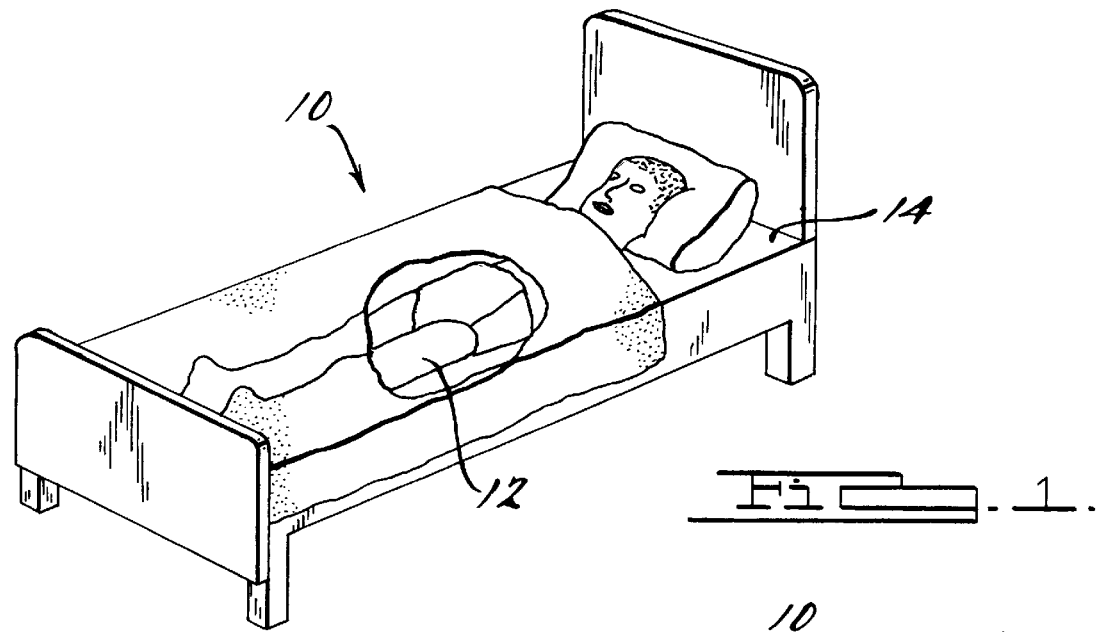
FIG. 1 is an elevational view of a diaper for eliminating bed sores, according to the present invention, illustrate in operational relationship with a person lying in a bed.
Figure 2:
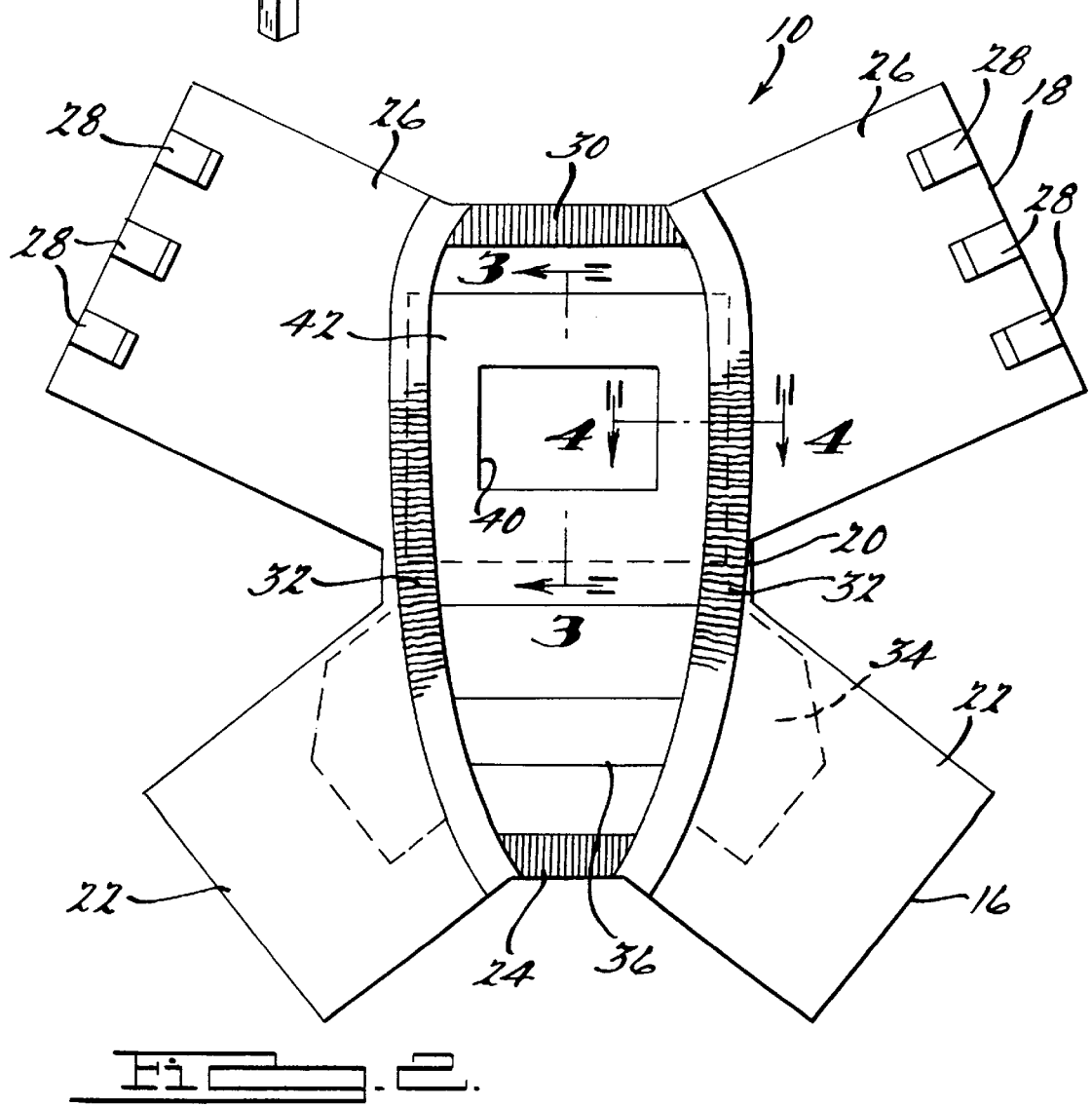
FIG. 2 is a top view of the diaper for eliminating bed sores of FIG. 1.

Referring now to the drawings and in particular FIGS. 1 and 2, one embodiment of a diaper 10 for eliminating bed sores, according to the present invention, is illustrated in operational relationship with a person 12 lying in a bed 14. The diaper 10 includes a front section 16, a back section 18, and a middle section 20. The front section 16 has a pair of front flanges 22 extending outwardly an angle to form a generally inverted "V" shape. The front flanges 22 are generally rectangular in shape. The front section 16 also includes an elastic member 24 extending between laterally between the front flanges 22 to allow the front flanges 22 to be extended away from each other laterally when wrapped around the person. It should be appreciated that the front section 16 is similar to that of a conventional disposable diaper.

The back section 18 has a pair of back or rear flanges 26 extending outwardly an angle to form a generally "V" shape. The back flanges 26 are generally rectangular in shape. Each of the back flanges 26 includes at least one, preferably a plurality of attachment members or tabs 28 secured thereto for attaching the back flanges 26 with the front flanges 22 to hold the diaper 10 to the body of the person 12 when the diaper 12 is in use. The attachment members 28 include an adhesive to allow the attachment members 28 to be folded back upon them when not in use and unfolded outwardly to adhesively attach themselves to the front flanges 22. The back section 18 also includes an elastic member 30 extending between laterally between the back flanges 26 to allow the back flanges 26 to be extended away from each other laterally when wrapped around the person.

The middle section 20 extends longitudinally between the front section 16 and back section 18. The middle section 16 is generally of a rectangular shape and smaller than and integrally disposed between the front and back sections 16 and 18, respectively. The middle section 20 includes an elastic member trim 32 extending longitudinally between the front and back sections 16 and 18, respectively, such that the middle section 20 defines a pair of lateral openings for legs of the person when the diaper 10 is in use. The middle section 20 also includes an absorbent layer or body 34 extending longitudinally between the elastic member 24 and 30 of the front section 16 and rear section 30, respectively.

Referring to FIGS. 2 through 4, each of the sections 16,18,20 has a liquid-permeable inner sheet 36 and a liquid-impermeable outer sheet 38 aligned with and peripherally secured to the inner sheet 36. The absorbent body 34 is disposed between and secured within the inner and outer sheets 36 and 38 from a middle to a front of the diaper 10. It should be appreciated that the inner sheet 36 lies proximal to a body of the person 12 when the diaper 10 is in use.

The diaper 10 further includes an aperture 40 extending through the inner sheet 36, absorbent body 34 an outer sheet 39 in a rear portion of the middle section 20. The aperture 40 is centrally located and generally rectangular in shape. In another embodiment (not shown), the diaper 10 may include a fluid-penetrable covering (not shown) disposed over the aperture 40 on outer sheet 38. The fluid-penetrable covering permits air to flow to an infected area of the skin of the person 12 while protecting the area from particulate matter, such as dust and the like. It should be appreciated that the aperture 40 may have any suitable shape and located off center or enlarged on one side relative to an opposed side as desired.

The diaper 10 includes a thickened area or portion 42 surrounding the aperture 40 and disposed within a portion thereof between the inner and outer sheets 36 and 38, respectively. The thickened portion 42 has a thickness greater than a thickness of the inner sheet 38, absorbent body 34 and outer sheet 38. The thickened portion 42 includes a cushioning layer or body 44 disposed in therein. The cushioning body 44 is made of a closed cell material such as a bubble wrap or film. The cushioning body 44 is generally cylindrical in shape. The thickened portion 42 also includes the absorbent body 34 disposed between the cushioning body 44 and the outer sheet 38. The thickened portion 42 further includes a fastening mechanism 46 such as adhesive tape to hold the cushioning body 44 in its cylindrical shape and to secure the inner sheet 36 to the cushioning body 44 and the outer sheet 38 to the cushioning body 44. It should be appreciated that the bubble wrap and tape are conventional and commercially known.

In operation of the diaper 10, the diaper 10 is attached to the person 12 in a normal manner. The middle section 20 is disposed between the legs of the person 12 with the front section 16 disposed in front of the body of the person 12 and the back section 18 disposed in back of the body of the person 12. The aperture 40 is located over any bed sore on the person and the front flanges 22 and back flanges 26 are extended toward each other around the body of the person 12. The attachment tabs 28 are unfolded from the back flanges 26 and attached to the front flanges 22 to hold the diaper 10 on the person 12. The thickened portion 42 elevates the skin of the person 12 away from the bed 14 and the absorbent body 34 absorbs any moisture to eliminate shin from being in contact with moisture that could cause the skin to decay.

Referring to FIGS. 5 through 8, a method, according to the present invention, of making the diaper 10 is shown. The method is directed to transforming a standard or conventional integral, absorbent, disposable diaper into the diaper 10 for eliminating bed sores. As illustrated in FIG. 5, a standard integral, absorbent, disposable diaper is generally indicated at 50 and partially shown. The method includes placing a desired outline 52 for the aperture 40 to surround a bed sore on a body of the person 12 on the outside of the outer sheet 38 at a rear portion of the middle section 20. The method includes cutting or slitting along crisscross slits 54 within and extending to the outline 52 through the outer sheet 38, absorbent body 34 and inner sheet 36 and forming respective cut tabs or portions 55 and 56 thereof. It should be appreciated that the slits 54 form an "X" shape and is cut through all layers of the diaper 50.

As illustrated in FIG. 6, the method includes lifting and separating the cut portions 54 and 56 of the outer sheet 38 and the inner sheet 36 from the absorbent body 34. Next, the method includes forming the material for the cushioning body 44 to a desired diameter and placing the cushioning body 44 between the cut portions 55,56 of the inner and outer sheets 36,38, respectively, and secured together by a fastening mechanism such as tape 58, for example, thereby forming a frame 60. In the preferred embodiment, the frame 60 is made of sheets of bubble packaging-film and has a generally rectangular shape.

As illustrated in FIG. 7, the method includes wrapping the cut portions 55,56 of the inner and outer sheets 36 and 38, respectively, wrapped around the frame 60, thereby forming the aperture 40 around which the frame 60 lies. As illustrated in FIG. 8, the method includes securing the cut portions 55,56 of the inner and outer sheets 36 and 38, respectively, to the frame 60 by the tape 58 to form the diaper 10.

Accordingly, the diaper 10 of the present invention overcomes the disadvantages in the related art by providing a disposable diaper to relieve bed sores. The diaper 10 has a thickened portion 42 around an aperture 40 for surrounding and protecting a bed sore on a person's body while that person is confined to a bed or chair. The thickened portion 42 lifts the sore and surrounding skin away from the bed or chair, thereby allowing the sore to heal by permitting air to and avoiding pressure on the sore. Since the sores can vary in severity, location, size, and, shape from person to person, the thickened portion 42 of the present invention can also include a variety of materials, locations, shapes, and sizes. As such, the aperture 40 can vary in size and dimension, too. Also, the fastening mechanism 46 can be tape or the like.

The present invention has been described in an illustrative manner. It is to be understood that the terminology, which has been used, is intended to be in the nature of words of description rather than of limitation.

Many modifications and variations of the present invention are possible in light of the above teachings. Therefore, within the scope of the appended claims, the present invention may be practiced other than as specifically described.

What is claimed is:

1. A diaper to eliminate bed sores comprising:

a front section;

a back section;

a middle section extending longitudinally between said front section and said back section;

said middle section comprising a liquid-permeable inner sheet, a liquid-impermeable outer sheet aligned with and secured to said inner sheet, and an absorbent body disposed between said inner sheet and said outer sheet;

said middle section including an aperture extending through said inner sheet and said absorbent body and said outer sheet and having a thickened portion including a cushioning body formed to a predetermined thickness completely surrounding said aperture, said aperture is adapted to be located over a bed sore on a body of person with said middle portion disposed between legs of the person and said front section disposed in front of the person and said back section disposed in back of the person and attached to said front portion when said diaper is in use.

2. A diaper as set forth in claim 2 wherein said cushioning body comprises a bubble wrap or film.

3. A diaper as set forth in claim 1 wherein said thickened portion includes said absorbent body disposed between said cushioning body and said outer sheet.

4. A diaper as set forth in claim 1 wherein said aperture is generally rectangular in shape.

5. A diaper as set forth in claim 1 including a fastening mechanism to secure said outer sheet and said inner sheet to said thickened portion.

6. A diaper as set forth in claim 5 wnerein said fastening mechanism is tape.

7. A diaper as set forth in claim 1 wherein said inner sheet and said outer sheet are wrapped over a portion of said thickened portion.

8. A diaper as set forth in claim 1 wherein aperture is located in a rear portion of said middle section.

\* \* \* \* \*